(12) United States Patent
Laloi et al.

(10) Patent No.: US 7,176,012 B2
(45) Date of Patent: Feb. 13, 2007

(54) CARBOXYPEPTIDASE OF COCOA

(75) Inventors: Maryse Laloi, Lausanne (CH); James McCarthy, Noizay (FR); Peter Bucheli, Shanghai (CN)

(73) Assignee: Nestec S.A., Vevey (CH)

( * ) Notice: Subject to any disclaimer, the term of this patent is extended or adjusted under 35 U.S.C. 154(b) by 502 days.

(21) Appl. No.: 10/382,239

(22) Filed: Mar. 5, 2003

(65) Prior Publication Data

US 2003/0219511 A1 Nov. 27, 2003

Related U.S. Application Data

(63) Continuation-in-part of application No. PCT/EP02/07162, filed on Jun. 28, 2002.

(30) Foreign Application Priority Data

Jul. 6, 2001 (EP) .................. 01116407

(51) Int. Cl.
- *C12N 9/48* (2006.01)
- *C12N 9/00* (2006.01)
- *C12N 1/20* (2006.01)
- *C12N 15/00* (2006.01)
- *C07H 21/04* (2006.01)

(52) U.S. Cl. .................. 435/212; 435/183; 435/252.3; 435/320.1; 536/23.2

(58) Field of Classification Search ............... 435/183, 435/212, 252.3, 320.1; 536/23.2
See application file for complete search history.

(56) References Cited

U.S. PATENT DOCUMENTS 5,888,562 A 3/1999 Hansen et al. ................. 426/45

FOREIGN PATENT DOCUMENTS

EP 0 749 694 A1 12/1996

OTHER PUBLICATIONS

Li et al. Accession AY072822. Dec. 4, 2002.*
Bytof et al., XP001037343, "Specificity and stability of the carboxypeptidase activity in ripe, undgerminated seeds of *Theobroma cacao* L.", Food Chemistruy, vol. 54, No. 1, pp. 15-21 (1995).
Blinkovsky et al, "Purification, characterization and heterologous expression in *Fusarium venenatum* of a novel serine carboxypeptidase from *Aspergillus oryzae*", Applied and Enginronmental Microbiology, vol. 65, No. 8 pp. 3298-3303 (1999).
Voigt et al, XP002106204, In-vitro formation of cocoa-specific aroma precursors: aroma-related peptides generated from cocoa-seed protein by cooperation of an aspartic endoprotease and a coarboxypeptidase' Food Chemistry, Elsevier Science Publishers Ltd. GB, vol. 49, No. 2, pp. 173-180 (1994).
Amin et al., XP001026129"Proteolytic actiivty (aspartic endoproteinase and carboxypeptidase) of cocoa bean during fermentation", Journal of the Science of Food and Agriculture, vol. 76, No. 1, pp. 123-128 (1998).

* cited by examiner

*Primary Examiner*—Tekchand Saidha
*Assistant Examiner*—Christian L. Fronda
(74) *Attorney, Agent, or Firm*—Bell, Boyd & Lloyd LLP

(57) ABSTRACT

The present invention relates to a novel carboxypeptidase gene and the polypeptide encoded thereby. In particular, the present invention relates to the use of the present carboxypeptidase and polypeptide in the manufacture of cocoa flavor and/or chocolate.

7 Claims, 4 Drawing Sheets

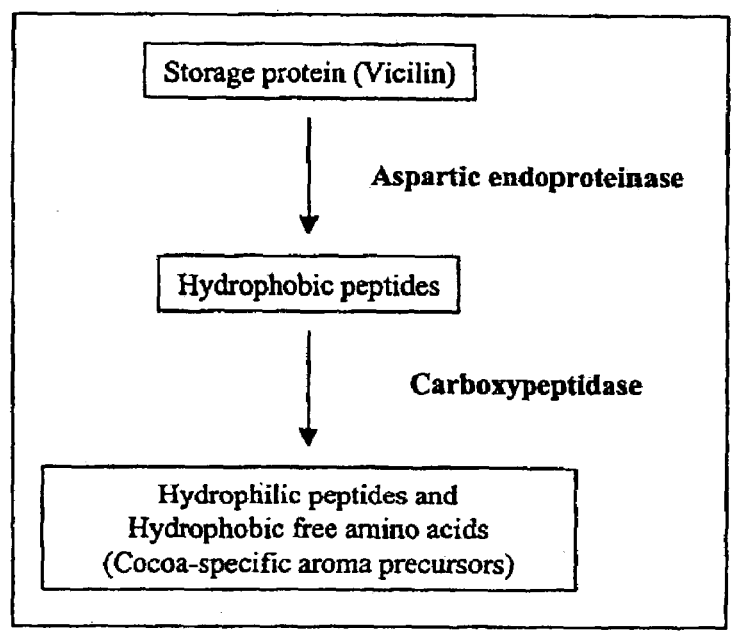
Figure 1: Proteolytic formation of the cocoa-specific aroma

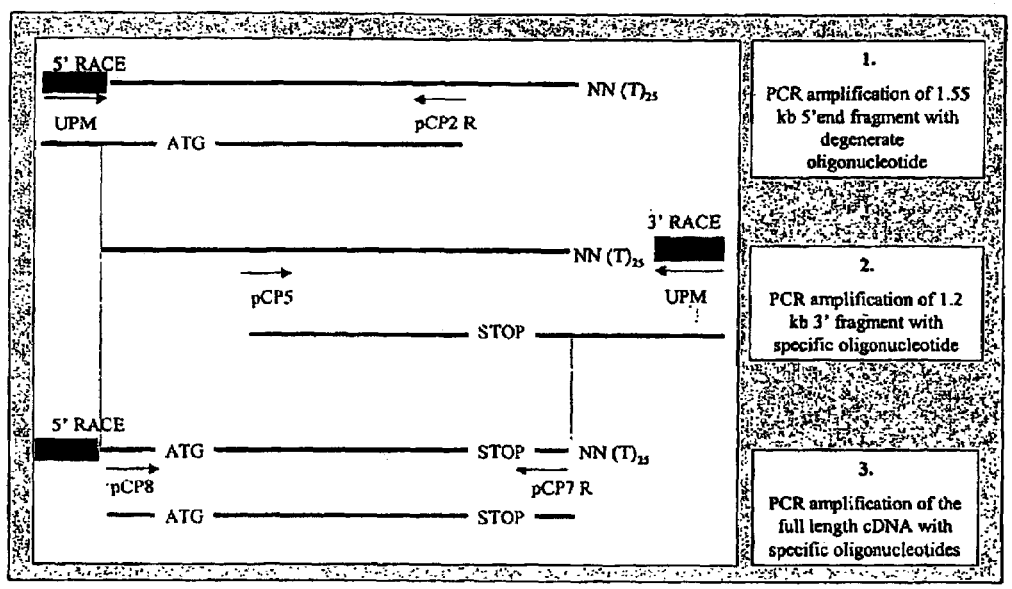
Figure 2: Cloning strategy used for the isolation of a cDNA encoding a carboxypeptidase from Theobroma cacao, clone ICS 95.

— Cacao    — Barley CP-MI
Residues position

— Cacao    — Barley CP-MII
Residues position

— Cacao    — Barley CP-MIII
Residues position

SEQUENCE LISTING

```
<160> NUMBER OF SEQ ID NOS: 6

<210> SEQ ID NO 1
<211> LENGTH: 1768
<212> TYPE: DNA
<213> ORGANISM: Theobroma cacao

<400> SEQUENCE: 1
gactctcaaa gagaaaaaga aaagatggca aatccgaaaa tcttataccc gttttctgtt      60
tcccttctct tcctcatttc catctcctcc gcggccgctt cctccttctt agacgagcgg     120
cgactcggag gatcaagttt ccccctcgata catgcgaaga agttgataag ggagttgaat     180
ttgtttccta aggaggaagt caacgtcgtt gatggaggcc aggtttcctt accggaggat     240
tcgaggttgg tggagaagcg gttcaagttc ccgaatttgg cggtgcctgg tggggtttcc     300
gttgaggatt tgggtcatca tgctggttat tacaagctag ctaattctca tgatgccaga     360
atgttctatt tcttctttga atcacgaaat agcaaaaagg accctgttgt aatctggttg     420
actggagggc cagggtgtag tagtgaattg gcttttgtttt atgaaaatgg tcctttttacc    480 attgctgaga acatgtctct tatttggaat cagtatggtt gggacatggc atcaaacctt     540
ctgtatgtgg accaacccat tggtaccggc tttagttata gttctgatag aagggacatt     600
cgtcataatg aagatgaagt tagcaacgac ctatatgact tcttacaggc attctttgct     660
gaacaccctg agtttgaaaa gaatgacttt tatataactg gagaatcata tgctgggcac     720
tacattccag cttttgctgc ccgagtccac caaggaaaca aagctaaaga tggaattcat     780
ataaacctaa agggatttgc tattggtaat ggcctgactg accctgcaat ccagtataaa     840
gcttacacag attatgcttt ggacatgggg gtaattaaga agtctgacta caatcgtatc     900
aacaagctgg ttccagtttg tgaaatggca ataaagcttt gtggcactga tggcacaatc     960
tcttgcatgg cttcatattt tgtctgcaat gccatattca ctggcatcat ggcacttgct    1020
ggcgatacaa attactacga cattagaacg aaatgtgaag ggagcctttg ctatgacttc    1080
tcaaacatgg agacatttct gaaccaggaa tctgttaggg atgcccttgg agttgggagt    1140
attgactttg tgtcctgcag tcctacagtg tatcaggcca tgctggttga ctggatgagg    1200
aatcttgaag ttggcattcc tgctctcctt gaggatggtg tcaagcttct tgtatatgct    1260
ggagaatatg atctcatctg caactggctt ggcaattcga gatgggtcca tgcaatgaaa    1320
tggtctggtc agaaggagtt tgtagcatct cctgaggttc cttttgtcgt tgatggctca    1380
gaagcaggag tcttgagaac tcatggacct cttggttttcc taaaggttca cgatgcaggt    1440
cacatggttc ctatggacca gccaaaggca gcattggaga tgctgaagcg gtggactaag    1500
```

-continued

```
ggtacattat ctgaagctgc cgattcagag aaattggttg ctgaaatatg atttccatca      1560
ttgcactgct tgcatacaat ttagttggca ttagaatggg aatagccgta tcgtaaagct      1620
ctggggtttc tatgtatgcc tgtaaataat tgcatgttaa tgctagtaca atggtatctt      1680 tgtttttga agatcaccta ctgaacttat atgaatcaag gacttataaa aatcttctaa       1740
aaaaaaaaaa aaaaaaaaaa aaaaaaa                                          1768
```

<210> SEQ ID NO 2
<211> LENGTH: 508
<212> TYPE: PRT
<213> ORGANISM: Theobroma cacao

<400> SEQUENCE: 2

```
Met Ala Asn Pro Lys Ile Leu Tyr Pro Phe Ser Val Ser Leu Leu Phe
 1               5                  10                  15

Leu Ile Ser Ile Ser Ser Ala Ala Ser Ser Phe Leu Asp Glu Arg
                20                  25                  30

Arg Leu Gly Gly Ser Ser Phe Pro Ser Ile His Ala Lys Lys Leu Ile
            35                  40                  45

Arg Glu Leu Asn Leu Phe Pro Lys Glu Val Asn Val Val Asp Gly
    50                  55                  60

Gly Gln Val Ser Leu Pro Glu Asp Ser Arg Leu Val Glu Lys Arg Phe
65                  70                  75                  80

Lys Phe Pro Asn Leu Ala Val Pro Gly Gly Val Ser Val Glu Asp Leu
                85                  90                  95

Gly His His Ala Gly Tyr Tyr Lys Leu Ala Asn Ser His Asp Ala Arg
            100                 105                 110

Met Phe Tyr Phe Phe Phe Glu Ser Arg Asn Ser Lys Lys Asp Pro Val
        115                 120                 125

Val Ile Trp Leu Thr Gly Gly Pro Gly Cys Ser Ser Glu Leu Ala Leu
    130                 135                 140

Phe Tyr Glu Asn Gly Pro Phe Thr Ile Ala Glu Asn Met Ser Leu Ile
145                 150                 155                 160

Trp Asn Gln Tyr Gly Trp Asp Met Ala Ser Asn Leu Leu Tyr Val Asp
                165                 170                 175

Gln Pro Ile Gly Thr Gly Phe Ser Tyr Ser Ser Asp Arg Arg Asp Ile
            180                 185                 190

Arg His Asn Glu Asp Glu Val Ser Asn Asp Leu Tyr Asp Phe Leu Gln
        195                 200                 205

Ala Phe Phe Ala Glu His Pro Glu Phe Glu Lys Asn Asp Phe Tyr Ile
    210                 215                 220

Thr Gly Glu Ser Tyr Ala Gly His Tyr Ile Pro Ala Phe Ala Ala Arg
225                 230                 235                 240

Val His Gln Gly Asn Lys Ala Lys Asp Gly Ile His Ile Asn Leu Lys
                245                 250                 255

Gly Phe Ala Ile Gly Asn Gly Leu Thr Asp Pro Ala Ile Gln Tyr Lys
            260                 265                 270

Ala Tyr Thr Asp Tyr Ala Leu Asp Met Gly Val Ile Lys Lys Ser Asp
        275                 280                 285

Tyr Asn Arg Ile Asn Lys Leu Val Pro Val Cys Glu Met Ala Ile Lys
    290                 295                 300

Leu Cys Gly Thr Asp Gly Thr Ile Ser Cys Met Ala Ser Tyr Phe Val
305                 310                 315                 320

Cys Asn Ala Ile Phe Thr Gly Ile Met Ala Leu Ala Gly Asp Thr Asn
```

-continued

```
                                325                 330                 335
Tyr Tyr Asp Ile Arg Thr Lys Cys Glu Gly Ser Leu Cys Tyr Asp Phe
            340                 345                 350
Ser Asn Met Glu Thr Phe Leu Asn Gln Glu Ser Val Arg Asp Ala Leu
        355                 360                 365
Gly Val Gly Ser Ile Asp Phe Val Ser Cys Ser Pro Thr Val Tyr Gln
        370                 375                 380
Ala Met Leu Val Asp Trp Met Arg Asn Leu Glu Val Gly Ile Pro Ala
385                 390                 395                 400
Leu Leu Glu Asp Gly Val Lys Leu Leu Val Tyr Ala Gly Glu Tyr Asp
                405                 410                 415
Leu Ile Cys Asn Trp Leu Gly Asn Ser Arg Trp Val His Ala Met Glu
            420                 425                 430
Trp Ser Gly Gln Lys Glu Phe Val Ala Ser Pro Glu Val Pro Phe Val
            435                 440                 445
Val Asp Gly Ser Glu Ala Gly Val Leu Arg Thr His Gly Pro Leu Gly
        450                 455                 460
Phe Leu Lys Val His Asp Ala Gly His Met Val Pro Met Asp Gln Pro
465                 470                 475                 480
Lys Ala Ala Leu Glu Met Leu Lys Arg Trp Thr Lys Gly Thr Leu Ser
                485                 490                 495
Gln Ala Ala Asp Ser Glu Lys Leu Val Ala Glu Ile
            500                 505
```

<210> SEQ ID NO 3
<211> LENGTH: 20
<212> TYPE: DNA
<213> ORGANISM: Artificial Sequence
<220> FEATURE:
<223> OTHER INFORMATION: Description of Artificial Sequence: Primer
<220> FEATURE:
<221> NAME/KEY: misc_feature
<222> LOCATION: (12)..(12)
<223> OTHER INFORMATION: any
<220> FEATURE:
<221> NAME/KEY: misc_feature
<222> LOCATION: (15)..(15)
<223> OTHER INFORMATION: any

<400> SEQUENCE: 3
ggytgrtcca tnggnaccat                                               20

<210> SEQ ID NO 4
<211> LENGTH: 22
<212> TYPE: DNA
<213> ORGANISM: Artificial Sequence
<220> FEATURE:
<223> OTHER INFORMATION: Description of Artificial Sequence: Primer

<400> SEQUENCE: 4
gcttttgctg cccgagtcca cc                                            22

<210> SEQ ID NO 5
<211> LENGTH: 23
<212> TYPE: DNA
<213> ORGANISM: Artificial Sequence
<220> FEATURE:
<223> OTHER INFORMATION: Description of Artificial Sequence: Primer

<400> SEQUENCE: 5
caaagagaaa aagaaaagat ggc                                           23

```
<210> SEQ ID NO 6
<211> LENGTH: 21
<212> TYPE: DNA
<213> ORGANISM: Artificial Sequence
<220> FEATURE:
<223> OTHER INFORMATION: Description of Artificial Sequence: Primer

<400> SEQUENCE: 6
ccccagagct ttacgatacg g                                            21
```

US 7,176,012 B2

CARBOXYPEPTIDASE OF COCOA

CROSS-REFERENCE TO RELATED APPLICATIONS

This application is a continuation-in-part of the US national phase designation of International application PCT/EP02/07162 filed Jun. 28, 2002, the content of which is expressly incorporated herein by reference thereto.

BACKGROUND ART

The present invention relates to a novel carboxypeptidase gene and the polypeptide encoded thereby. In particular, the present invention relates to the use of the present carboxypeptidase in the manufacture of cocoa flavor and/or chocolate.

It is known that in processing cacao beans the generation of the typical cocoa flavor requires two steps—a fermentation step, which includes air-drying of the fermented material, and a roasting step.

During fermentation two major activities may be observed. First, the pulp surrounding the beans is degraded by micro-organisms with the sugars contained in the pulp being largely transformed to acids, especially acetic acid (Quesnel et al., J. Sci. Food. Agric. 16 (1965), 441–447; Ostovar and Keeney, J. Food. Sci. 39 (1973), 611–617). The acids then slowly diffuse into the beans and eventually cause an acidification of the cellular material. Second, fermentation also results in a release of peptides exhibiting differing sizes and a generation of a high level of hydrophobic free amino acids. This latter finding led to the hypothesis that proteolysis occurring during the fermentation step is not due to a random protein hydrolysis but seems to be rather based on the activity of specific endoproteinases (Kirchhoff et al., Food Chem 31 (1989), 295–311). This specific mixture of peptides and hydrophobic amino acids is deemed to represent cocoa-specific flavor precursors.

Until now several proteolytic enzyme activities have been investigated in cacao beans and studied for their putative role in the generation of cocoa flavor precursors during fermentation.

An aspartic endoproteinase activity, which is optimal at a very low pH (pH 3.5) and inhibited by pepstatin A has been identified. A polypeptide described to have this activity has been isolated and is described to consist of two peptides (29 and 13 kDa) which are deemed to be derived by self-digestion from a 42 kDa pro-peptide (Voigt et al., J. Plant Physiol. 145 (1995), 299–307). The enzyme cleaves protein substrates between hydrophobic amino acid residues to produce oligopeptides with hydrophobic amino acid residues at the ends (Voigt et al., Food Chem. 49 (1994), 173–180). The enzyme accumulates with the vicilin-class (7S) globulin during bean ripening. Its activity remains constant during the first days of germination and does not decrease before the onset of globulin degradation (Voigt et al., J. Plant Physiol. 145 (1995), 299–307).

Also a cysteine endoproteinase activity had been isolated which is optimal at a pH of about 5. This enzymatic activity is believed not to split native storage proteins in ungerminated seeds. Cysteine endoproteinase activity increases during the germination process when degradation of globular storage protein occurs. To date, no significant role for this enzyme in the generation of cocoa flavor has been reported (Biehl et al., Cocoa Research Conference, Salvador, Bahia, Brasil, Nov. 17–23, 1996).

Moreover, a carboxypeptidase activity has been identified which is inhibited by PMSF and thus belongs to the class of serine proteases. It is stable over a broad pH range with a maximum activity at pH 5.8. This enzyme does not degrade native proteins but preferentially splits hydrophobic amino acids from the carboxy-terminus of peptides (Bytof et al., Food Chem. 54 (1995), 15–21).

During the second step of cocoa flavor production—the roasting step—the oligopeptides and amino acids generated at the stage of fermentation are obviously subjected to a Maillard reaction with reducing sugars present in fermented beans eventually yielding substances responsible for the cocoa flavor as such.

In the art there have been many attempts to artificially produce cocoa flavor.

Cocoa-specific aroma has been obtained in experiments wherein acetone dry powder (AcDP) prepared from unfermented ripe cacao beans was subjected to autolysis at a pH of 5.2 followed by roasting in the presence of reducing sugars. It was conceived that under these conditions preferentially free hydrophobic amino acids and hydrophilic peptides should be generated and the peptide pattern thus obtained was found to be similar to that of extracts from fermented cacao beans. An analysis of free amino acids revealed that Leu, Ala, Phe and Val were the predominant amino acids liberated in fermented beans or autolysis (Voigt et al., Food Chem. 49 (1994), 173–180). In contrast to these findings, no cocoa-specific aroma could be detected when AcDP was subjected to autolysis at a pH of as low as 3.5 (optimum pH for the aspartic endoproteinase). Only few free amino acids were found to be released but a large number of hydrophobic peptides were formed. When peptides obtained after the autolysis of AcDP at a pH of 3.5 were treated with carboxypeptidase A from porcine pancreas at pH 7.5, hydrophobic amino acids were preferentially released. The pattern of free amino acids and peptides was similar to that found in fermented cacao beans and to the proteolysis products obtained by autolysis of AcDP at pH 5.2. After roasting of the amino acids and peptides mixture as above, a cocoa aroma could be generated.

It has also been shown that, a synthetic mixture of free amino acids alone with a similar composition to that of the spectrum found in fermented beans, was incapable of generating cocoa aroma after roasting, indicating that both the peptides and the amino acids are important for this purpose (Voigt et al., Food Chem. 49 (1994), 173–180.

In view of the above data a hypothetical model for the generation, during fermentation, of the said mixture of peptides and amino acids, i.e. the cocoa flavor precursors, had been devised (FIG. 1), where in a first step peptides having a hydrophobic amino acid at their end, are formed from storage proteins, which peptides are then further degraded to smaller peptides and free amino acids. To produce the said peptides having C-terminal hydrophobic amino acids, an aspartic endoproteinase activity related to that mentioned above seems to be involved. Yet, for splitting off hydrophobic amino acids from peptides formed in the preceding step the only known enzymatic activity, which might be considered in this respect, is that of a carboxypeptidase. However, such enzyme has not been isolated and studied in detail in cacao and it is therefore still questionable, which cacao enzyme might be responsible for the generation of hydrophobic amino acids required for cocoa flavor.

Though some aspects of cocoa flavor production have been elucidated so far there is still a need in the art to fully understand the processes involved, so that the manufacture of cocoa flavor may eventually be optimized.

SUMMARY OF THE INVENTION

The present invention provides means for further elucidating the processes involved in the formation of cocoa-specific aroma precursors during the fermentation of cacao seeds, to improve the formation of cocoa flavor during processing and manufacturing and eventually providing means assisting in the artificial production of cocoa flavor.

This problem has been solved by providing a nucleotide sequence encoding a novel carboxypeptidase from cacao beans (termed cacao CP-III), which is identified by SEQ. ID. No. 1, or functional derivatives thereof having a degree of homology that is greater than 80%, preferably greater than 90% and more preferably greater than 95%.

It will be appreciated by the skilled person that a gene encoding a specific polypeptide may differ from a given sequence according to the Wobble hypothesis, in that nucleotides are exchanged that do not lead to an alteration in the amino acid sequence. Yet, according to the present invention also nucleotide sequences shall be embraced, which exhibit a nucleotide exchange leading to an alteration of the amino acid sequence, such that the functionality of the resulting polypeptide is not essentially disturbed.

This nucleotide sequence may be used to synthesise a corresponding polypeptide by means of recombinant gene technology, in particular a polypeptide as identified by SEQ. ID. No. 2.

As has been shown in a comparison with other carboxypeptidases from other plants the present enzyme does not show a substantial homology to any of the carboxypeptidases known so far. Since it is assumed, that cocoa may furthermore contain additional carboxypeptidases that might exhibit a higher homology to the carboxypeptidases known so far it must be considered as a surprising fact that this very enzyme has been detected.

For producing the polypeptide by recombinant means, the nucleotide of the present invention is included in an expression vector downstream of a suitable promoter and is subsequently incorporated into a suitable cell, which may be cultured to yield the polypeptide of interest. Suitable cells for expressing the present polypeptide include bacterial cells, such as e.g. *E. coli,* or yeast, insect, mammalian or plant cells.

The present DNA sequence may also be incorporated directly into the genome of the corresponding cell by techniques well known in the art, such as e.g. homologous recombination. Proceeding accordingly will provide a higher stability of the system and may include integration of a number of said DNA-sequences into a cell's genome.

The cells thus obtained may in consequence be utilized to produce the polypeptide in batch culture or using continuous procedures, with the resulting polypeptide being isolated according to conventional methods.

The recombinant carboxypeptidase obtained may be used for the manufacture of cocoa flavor. To this end, the enzyme described herein may be utilized in an artificial trial run, wherein a mixture of different proteins, such as cacao storage proteins, or protein hydrolysates of other resources, are subjected to enzymatic degradation by means of enzymes, known to be involved in proteolytic degradation to eventually assist in the production of flavor precursors. The enzyme may likewise also be utilized in the production of cocoa liquor, and in the manufacture of chocolate.

Yet, the present invention also provides plants, in particular cacao plants, comprising a recombinant cell, containing one or more additional copies of the carboxypeptidase of the present invention. Such a cacao plant will produce beans, which will exhibit a modified degradation of storage proteins when subjected to the fermentation process, allowing a more rapid degradation or a pattern of hydrolysis that yields a higher level of cocoa flavor precursor, since a higher amount of carboxypeptidase will be present.

The carboxypeptidase of the present invention may also be used to produce other transgenic plants such as soybean and rice, producing seeds with this new protein modifying enzyme.

BRIEF DESCRIPTION OF THE DRAWING FIGURES

In the figures,

FIG. 1 shows a scheme illustrating a potential process for the proteolytic formation of cocoa-specific aroma;

FIG. 2 shows the cloning strategy used for the isolation of a cDNA encoding a carboxypeptidase from *Theobroma cacao;*

DETAILED DESCRIPTION OF THE PREFERRED EMBODIMENTS

Figure 3A:
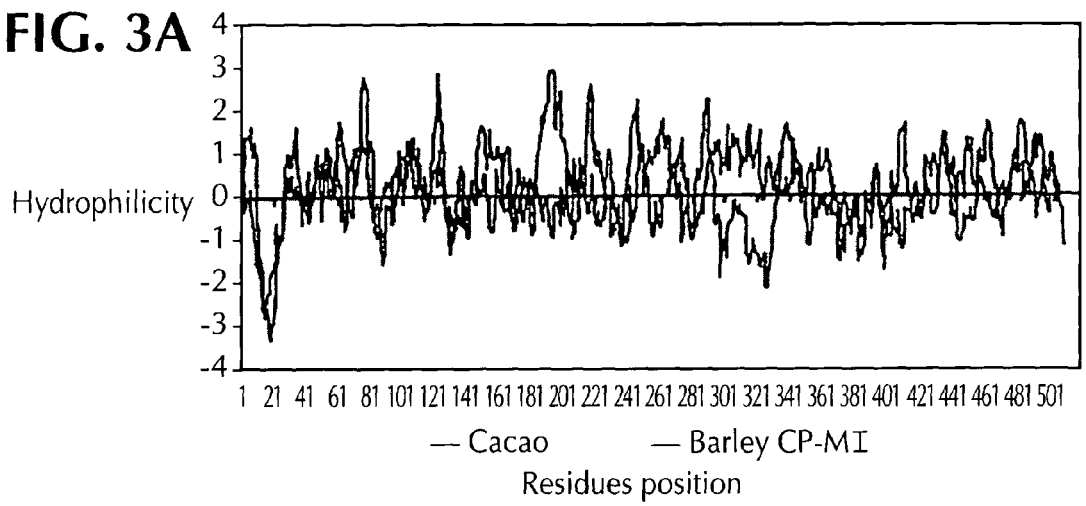
FIG. 3 shows a comparison of the hydrophilicity Plot-Kyte-Doolittle for the cacao CP-III sequence with Barley CP-MI, CP-MII and CP-MIII.

As described above, it was suggested that a carboxypeptidase could be involved in the production of cocoa flavor precursors during cacao fermentation. However it was not known in the art which cacao carboxypeptidase carried out this function considering that five classes of carboxypeptidases (Type I-V) have been identified in different plants by references to differences in substrate specificities, molecular weights and chromatographic profiles. Furthermore 50 sequences having homologies with serine carboxypeptidases exist in the completed *Arabidopsis* genome.

The proteolytic formation of cocoa-specific aroma according to the invention is illustrated in FIG. 1.

The following examples illustrate the invention further without limiting it thereto. In the examples the following abbreviations have been used:

PCR: Polymerase Chain Reaction
RACE: Rapid Amplification cDNA Ends
cDNA: complementary deoxyribonucleic acid
mRNA: messenger ribonucleic acid
DEPC: Diethyl pyrocarbonate
3,4-DCI: 3,4-dichloroisocoumarin

EXAMPLES

Materials

Cacao (*Theobroma cacao* L.) seeds (male parent unknown) from ripe pods of clone ICS 95 were provided by Nestlé ex-R&D Center Quito (Ecuador). The seeds were taken from the pods immediately after arrival at Nestle Research Center Tours (4–5 days after harvesting). The pulp and the seed coat were eliminated and the cotyledons were frozen in liquid nitrogen and stored at −80° C. until use.

Preparation of mRNA

Total RNA was prepared using the following method. Two seeds were ground in liquid nitrogen to a fine powder and extraction was directly performed with a lysis buffer containing 25 mM Tris HCl pH8, 25 mM EDTA, 75 mM NaCl, 1% SDS and 1M β-mercaptoethanol. RNA was extracted with one volume of phenol/chloroform/isoamylalcohol (25/24/1) and centrifuged at 8000 rpm, 10 min at 4° C. The aqueous phase was extracted a second time with one volume of phenol/chloroform/isoamylalcohol (25/24/1). RNA was precipitated with 2M lithium chloride at 4° C. overnight. The RNA pellet obtained after centrifugation was resuspended in DEPC treated water and a second precipitation with 3M sodium acetate pH 5.2 was performed in presence of two volumes of ethanol. The RNA pellet was washed with 70% ethanol and resuspended in DEPC treated water. Total RNA was further purified using the Rneasy Mini kit from Qiagen®.

Cloning of a carboxypeptidase cDNA

Cloning Strategy

A 1.5 kb 5' end fragment of a carboxypeptidase from cacao seed was amplified by RT-PCR using a degenerate oligonucleotide. Based on the sequence of this fragment, a primer was designed to amplify a 3'-end fragment. Finally, a full-length cDNA (cacao CP-III) was amplified using primers specific to both extremities. The cloning strategy used for isolation of a cDNA encoding a carboxypeptidase from Theobroma cacao, clone ICS 95 is shown in FIG. 2.

Primer Design

A search for carboxypeptidase sequences in the GenBank database lead to the identification of several plant sequences. A multiple alignment of these sequences revealed the presence of conserved regions. The conserved sequence MVP-MDQP located near the histidine catalytic site has been used to design a degenerate oligonucleotide in the antisense orientation: pCP2r (5'-GGYTGRTCCATNGGNACCAT) (SEQ ID No. 3).

Synthesis of cDNA

Total RNA (see above) was used to synthesise first strand 3' and 5' cDNAs with the SMART™ RACE cDNA Amplification Kit (Clontech, USA). Synthesis has been performed exactly as described in the kit instructions using 1 μg of total RNA and the Superscript™ II MMLV reverse transcriptase (Gibco BRL, USA). After synthesis, cDNAs were used directly for PCR or kept at −20° C.

5' RACE Amplification

Specific cDNA amplification was performed with 2.5 μl of the first strand 5' cDNA in 50 μl buffer containing: 40 mM Tricine-KOH pH 8.7, 15 mM KOAc, 3.5 mMMg(OAc)$_2$, 3.75 μg/ml BSA, 0.005% Tween-20, 0.005% Noninet-P40, 0.2 mM dNTP's, 14 pmoles of pCP2r primer, 5 μl of 10× Universal primer Mix (UPM) and 1 μl 50× Advantage 2 polymerase Mix (Clontech, USA). Amplification was performed in a Bio-med thermocycler 60 (B. Braun). A first denaturation step (94° C., 2 min) was followed by 35 cycles of denaturation (94° C., 1 min), primer annealing (55° C., 1.5 min) and extension (72° C., 2 min). The extension time was increased by 3 sec at each cycle. Amplification was ended by a final extension step (72° C., 10 min). The amplified fragment was cloned in pGEM®-T vector and sequenced.

3' RACE PCR

The sequence information obtained after the sequencing of the 5' end fragment was used to design a specific oligonucleotide pCP5 (5'-GCTTTTGCTGCCCGAGTC-CACC) (SEQ ID No. 4), which was used for 3'-RACE amplification. 3'-RACE PCR was performed with 2.5 μl of SMART single strand 3' cDNA in 50 μl buffer containing 40 mM Tricine-KOH pH 8.7, 15 mM KOAc, 3.5 mM Mg(OAc)$_2$, 3.75 μg/ml BSA, 0.005% Tween-20, 0.005% Nonidet-P40, 0.2 mM dNTP's, 10 pmoles of pCP5 primer, 10 μl of 10× Universal primer Mix (UPM) and 1 μl 50 × Advantage 2 polymerase Mix (Clontech, USA). Amplification was performed via touchdown PCR, in a Bio-med thermocycler 60 (B. Braun).

A first denaturation step (94° C., 1 min) was followed by:

5 cycles including denaturation at 94° C. for 30 sec and annealing/extension at 72° C. for 3 min 5 cycles including denaturation at 94° C. for 30 sec and annealing/extension at 70° C. for 30 sec and 72° C. for 3 min 30 cycles including denaturation at 94° C. for 30 sec and annealing/extension at 68° C. for 30 sec and 72° C. for 3 min.

The amplified fragment was cloned in PGEM®-T vector and sequenced.

Full Length cDNA

The sequence information obtained after the sequencing of 5'-and 3'-RACE fragments was used to design two specific oligonucleotides.

pCP8: A sense primer (5'-CAAAGAGAAAAAGAAAA-GATGGC) (SEQ ID No. 5)

pCP7r: A reverse primer (5'-CCCCAGAGCTTTAC-GATACGG) (SEQ ID No. 6).

PCR reaction was performed with 2.5 μl first strand cDNA in 50 μl buffer containing: 40 mM Tricine-KOH pH 8.7, 15 mM KOAc, 3.5 mM Mg(OAc)$_2$, 3.75 μg/ml BSA, 0.005% Tween-20, 0.005% Noninet-P40, 0.2 mM dNTP's, 10 pmoles of pCP8 primer, 10 pmoles of pCP7r primer and 1 μl 50× Advantage 2 polymerase Mix (Clontech, USA). Amplification was performed in a Bio-med thermocycler 60 (B. Braun). A first denaturation step (94° C., 1 min) was followed by 35 cycles of denaturation (94° C., 30 sec), primer annealing (63° C., 1 min) and extension (72° C., 2 min). The extension time was increased by 3 see at each cycle. Amplification was ended by a final extension step (72° C., 10 min). The amplified fragment was cloned in pGEM®-T Easy vector and sequenced.

Sequencing and Analysis of DNA Sequences cDNA sequencing has been performed by Eurogentech (Belgium) and ESGS (France). Sequence analysis and comparison were performed with Lion's software bioScout, Lasergene software (DNAStar) and Genedoc programme.

The cacao CP-III cDNA sequence is 1768 bp long. A putative initiation start codon was assigned by comparison with other carboxypeptidase sequences. It is located 25 bp from the 5' end. The open reading frame is broken by a stop codon (TGA) at position 1549, followed by a putative polyadenylation signal (TATAAA) at position 1725.

Figure 3B:
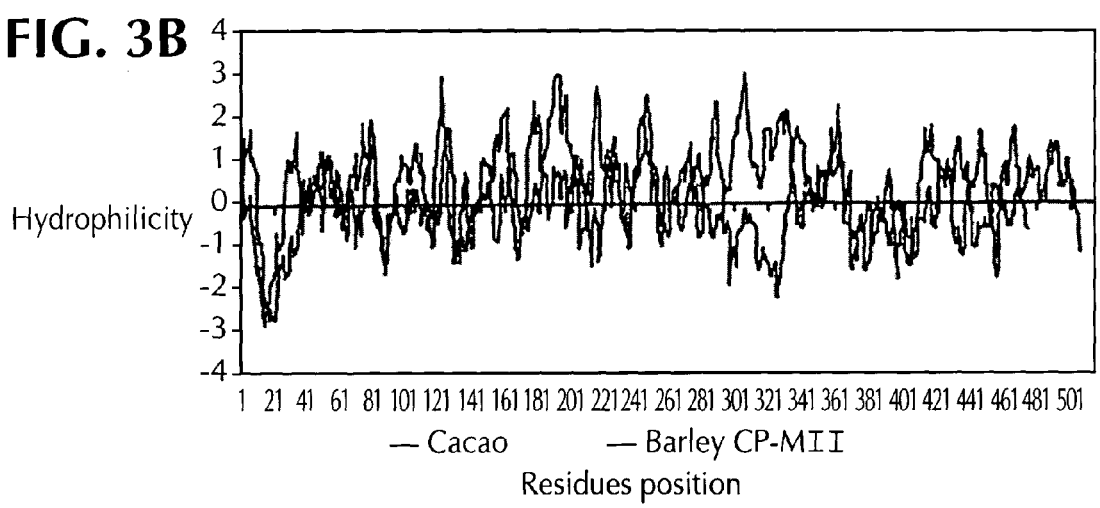
Figure 3C:
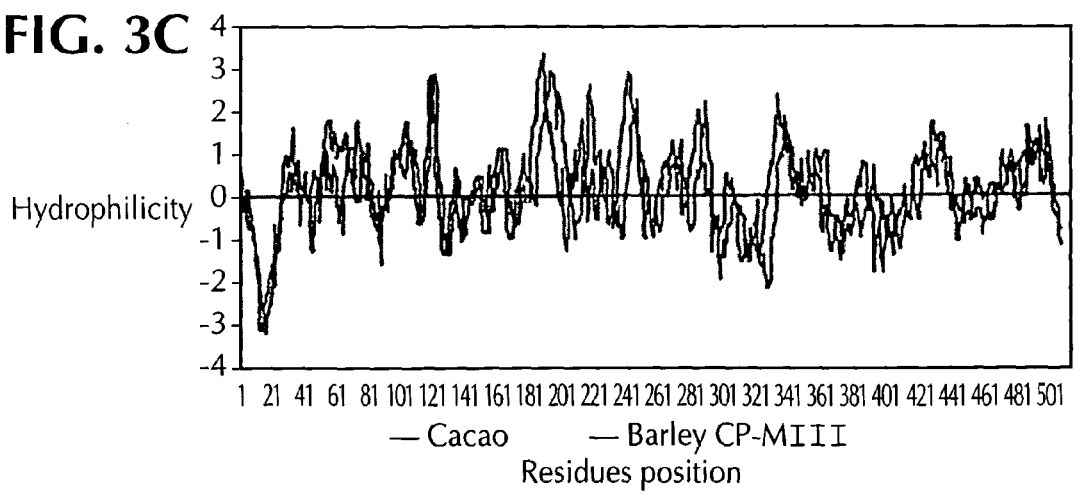

Cacao CP-III encodes a 508 amino acid type III carboxypeptidase C with a predicted molecular weight of 56 kDa and a pI of 5.04. The catalytic amino acids are present at position Ser$^{228}$, Asp$^{416}$ and His$^{473}$. A hydrophilicity analysis was performed using a Lasergene program (DNASTAR) and a window of 9. The results of a comparison of the hydrophilicity Plot-Kyte-Doolittle for the cacao CP-III sequence with Barley CP-ML CP-MII and CP-MIII (FIG. 3) reveals that cacao CP-III encodes a hydrophilic protein with a very hydrophobic N-terminal end, indicating the presence of a signal peptide.

Northern Blot Analysis

Figure 4A:
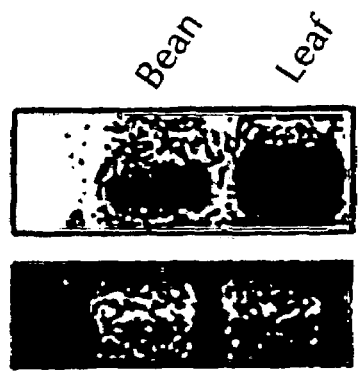
FIGS. 4A, 4B and 4C shows a Northern blot analysis of cacao CP-III.
Figure 4B:
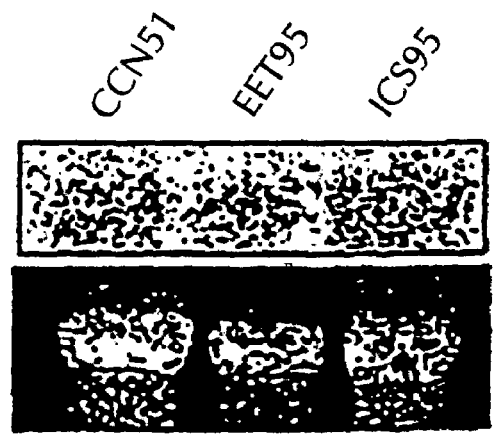
Figure 4C:

Total RNA samples were separated on 1.5% agarose gel containing 6% formaldehyde. RNA was separated on agarose gels, then transferred to a nylon membrane and probed with radiolabelled cacao CP-III cDNA under stringent hybridization conditions. An equal loading of the RNA samples was confirmed by ethidium bromide straining of ribosomal RNA in the gel before transfer to the membrane (FIG. 4). After electrophoresis, RNA was blotted onto nylon membranes (Appligene) and hybridized with $^{32}$P-labeled cacao CP-III probe at 65° C. in 250 mM Na-phosphate buffer pH 7.2, 6.6% SDS, 1 mM EDTA and 1% BSA. Cacao CP-III cDNA fragment was amplified by PCR using pCP8 and pCP7R primers and labelled by the random priming procedure (rediprime™ II, Amersham Pharmacia Biotech). Membranes were washed three times at 65° C. for 30 mm in 2×SSC, 0.1%SDS, in 1×SSC, 0.1% SDS and in 0.5×SSC, 0.1%SDS. FIG. 4A illustrates the total RNA (15 μg per lane) from seed and leaf. FIG. 4B illustrates the total mature seed (15 μg per lane)from different *T. cacao* clones while FIG. 4C illustrates total RNA (15 μg per lane) from seed at different stages of germination.

What is claimed is:

1. An isolated nucleotide sequence coding for a carboxypeptidase and comprising the nucleotide sequence of SEQ. ID. No. 1 or variants thereof having a degree of homology of more than 90% to SEQ. ID. No. 1, wherein said variants code for a carboxypeptidase.

2. A vector comprising the nucleotide sequence of claim 1.

3. An isolated cell comprising the nucleotide sequence of claim 1.

4. An isolated bacterial, yeast, insect, mammalian or plant cell comprising the nucleotide sequence of claim 1.

5. An isolated cacao cell comprising the nucleotide sequence of claim 1.

6. A method for recombinantly producing a carboxypeptidase comprising culturing the host cell of claim 3 in a medium under suitable conditions, and isolating the carboxypeptidase.

7. A recombinant nucleotide sequence coding for a carboxypeptidase and comprising the nucleotide sequence of SEQ. IID. No. 1 or variants thereof having a degree of homology of more than 90% to SEp. ID. No. 1, wherein said variants code for a carboxypeptidase.

* * * * *